United States Patent [19]

Siciliano

[11] Patent Number: 5,490,982
[45] Date of Patent: Feb. 13, 1996

[54] COSMETIC COMPOSITION

[75] Inventor: Marcina Siciliano, Naugatuck, Conn.

[73] Assignee: Elizabeth Arden Company, Division of Conopco, Inc., New York, N.Y.

[21] Appl. No.: 382,353

[22] Filed: Feb. 1, 1995

[51] Int. Cl.$^6$ ........................................ A61K 6/00
[52] U.S. Cl. .............. 424/401; 424/65; 424/73; 424/70.12
[58] Field of Search .................... 424/401, 65, 70.12, 424/73

[56] References Cited

U.S. PATENT DOCUMENTS

| | | | |
|---|---|---|---|
| 4,746,509 | 5/1988 | Haggiage et al. | 424/449 |
| 5,021,185 | 6/1991 | Mustakallio | 252/142 |
| 5,162,378 | 11/1992 | Guthauser et al. | 424/401 |
| 5,234,689 | 8/1993 | Lindauer et al. | 424/401 |
| 5,290,555 | 3/1994 | Guthauser et al. | 424/401 |
| 5,368,857 | 11/1994 | Corcoran et al. | 424/401 |
| 5,384,117 | 1/1995 | Vu et al. | 424/401 |

OTHER PUBLICATIONS

Solubilisant LRI Technical Bulletin–Dec. 1993.

*Primary Examiner*—Mark Sweet
*Attorney, Agent, or Firm*—Milton L. Honig

[57] ABSTRACT

A cosmetic microemulsion composition is provided including a fragrance and a vehicle system noninterfering with the fragrance scent and including water, isoeicosane and a $C_8$–$C_{40}$ fatty glyceride ester alkoxylated with from 1 to 100 moles $C_2$–$C_3$ alkylene oxide per mole of glyceride. These microemulsions are best utilized as aftershave balm with a fragrance identical if not at least quite similar to a signature perfume.

6 Claims, No Drawings

COSMETIC COMPOSITION

BACKGROUND OF THE INVENTION

1. Field of the Invention

The present invention relates to oil and water microemulsions formulated with fragrance, especially fragrance delivering aftershave balm.

2. The Related Art

Perfumes are often accompanied in the marketplace by an array of related cosmetics carrying the perfume family trademark. These cosmetics may be eau de toilette, cologne, antiperspirants/deodorants, shaving cream, body lotion and aftershave balm. Ordinarily, fragrances are specifically created for cosmetic products. Not so in the world of the signature perfume entourage product. Here the fragrance must be the same, or at least quite similar, to confirm association of perfume with the entourage product. For instance, Sunflowers®, Red Door®, Chloe Narcisse®, Calvin Klein®, Lagerfeld® or Elizabeth Taylor White Diamonds® perfumes would contribute their scent to a name related cosmetic formulation.

One name related product often accompanying a signature perfume is aftershave balm. Besides the fragrance, these balms are often formulated as an oil and water microemulsion, usually also containing at least one skinfeel agent. The skinfeel agent must be odor compatible with the fragrance. Moreover, this agent must impart a good afterfeel while being non-tacky and non-greasy, as well as being compatible with the microemulsion. The art is continually searching for formulations exhibiting improved performance within the aforedescribed criteria.

Accordingly, it is an object of the present invention to provide an improved cosmetic composition, especially an aftershave balm with fragrance in a carrier system having improved skinfeel properties.

Another object of the present invention is to provide an improved cosmetic composition, especially an aftershave balm with fragrance in a carrier system which does not interfere with the scent of the fragrance.

Still another object of the present invention is to provide an improved cosmetic composition, especially an aftershave balm with fragrance in a carrier system, in a visually clear microemulsion form.

These and other objects of the present invention will become more readily apparent from consideration of the following summary and detailed description.

SUMMARY OF THE INVENTION

A cosmetic microemulsion composition, especially an aftershave balm, is provided that includes:

(i) from 0.5 to 8% by weight of a fragrance;
(ii) from 30 to 80% of water;
(iii) from 0.5 to 8% by weight of isoeicosane; and
(iv) from 1 to 40% by weight of $C_8$–$C_{40}$ fatty glyceride ester alkoxylated with from 1 to 100 moles $C_2$–$C_3$ alkylene oxide per mole of glyceride.

DETAILED DESCRIPTION OF THE INVENTION

Emulsions are dispersed systems containing at least two immiscible liquid phases, one of which is dispersed in the form of small droplets throughout the other. Typically, one of the two immiscible liquids in an emulsion is aqueous while the other is an oil. Emulsions ordinarily tend to be opaque or white because of the large droplet size. Clear compositions require microemulsions. These consist of micelles of a monolayer of surfactant surrounding an oil droplet. These micelles are small enough so that they do not appreciably diffract light but instead produce a clear product. Clarity has been found to be quite dependent on the type and amounts of surfactant and skinfeel agents.

According to the present invention there is provided a microemulsion whose components have odor properties which would not interfere with a signature fragrance. Importantly, these components not only maintain clarity for the microemulsion but also provide a satisfactory afterfeel.

An essential element in compositions of this invention is a skinfeel agent which is isoeicosane, commercially available as Permethyl 99A available from the Permethyl Corporation, of Frazer, Pa. Amounts of the isoeicosane will range from 0.5 to 8%, preferably from 1 to 7%, optimally from 3 to 6% by weight.

A fragrance blend corresponding to the scent of a commercial signature perfume will also be found in compositions of this invention in amounts ranging from about 0.5 to about 8%, preferably from about 1 to about 4% by weight. The term "commercial signature perfume" is intended to mean a fragrance formulation emitting a pleasant odor and sold for such main purpose as a perfume. A fragrance formulation may include such components as $C_{10}$–$C_{30}$ terpenes, $C_5$–$C_{50}$ aldehydes, $C_5$–$C_{50}$ ketones, $C_5$–$C_{50}$ esters and combinations thereof. The following is a list of illustrative specific fragrance components:

iso-amyl salicylate,
carvacrol,
clove leaf oil,
ethyl salicylate,
iso-eugenol,
hexyl salicylate,
thyme oil red,
geraniol,
limonene,
6-acetyl-1,1,3,4,4,6-hexamethyl-tetrahydronaphthalene,
p-t-amyl cyclohexanone,
2-n-heptylcyclo-pentanone,
a-iso-methyl ionone,
β-methyl naphthyl ketone,
iso-butyl quinoline,
methyl anthranilate,
o-t-butylcyclohexyl acetate,
p-t-butylcyclohexyl acetate,
diethyl phthalate,
nonanediol-1,3-diacetate,
nonanolide-1,4,
i-nonyl acetate,
i-nonyl formate,
phenylethyl phenyl acetate,
cinnamic alcohol,
dimyrcetol,
hydroxymethyl isopropyl cyclopentane,
tetrahydromuguol,
cedar wood oil,
geranyl phenylacetate, guaiacwood oil,
linalyl benzoate,
phenyl ethyl alcohol,
dihydromyrcenol,
linalool,
isolongifolanone,
hexyl cinnamic aldehyde,
linalyl acetate,
citronellyl acetate,
phenyl ethyl acetate,
acetyl tributyl citrate,
benzyl salicylate,
isobutyl cinnamate,
linalyl cinnamate,
coumarin,
acetyl cedrene,
allyl amyl glycolate,
vanillin,
patchouli oil,
bergamot oil,
citronellol, and combinations thereof.

The nomenclature adopted for the components listed above, so far as possible, is that employed by Steffan Arctander in "Perfume and Flavor Chemicals (Aroma Chemicals)" Volume I and II (1969) and the "Perfume & Flavor Materials of Natural Origin" (1960) by the same author.

Compositions of this invention will contain water in amounts from 30 to 80%, preferably from 45 to 70%, optimally from 50 to 65% by weight.

A fourth essential element in compositions according to the present invention is that of a $C_8$–$C_{40}$ fatty glyceride ester alkoxylated with from 1 to 100 moles $C_2$–$C_3$ alkylene oxide per mole of glyceride, preferably from 4 to 20 moles alkylene oxide, optimally from 6 to 10 moles alkylene oxide per mole of glyceride.

The preferred alkylene oxides are ethylene oxide and propylene oxide. Amounts of this ester may range from 1 to 40%, preferably from 3 to 30%, optimally from 20 to 28% by weight of the composition. Illustrative of this category are PEG-6 caprylic/capric glyceride and PEG-8 caprylic/capric glyceride each of which are polyethylene glycol derivatives of a mixture of mono, di and triglycerides of caprylic and capric acids with a respective 6 and 8 moles of ethylene oxide. The higher alkoxylated ester is available from Gattefosse sold under the trademark of Labrasol. These esters have a combined surfactant and skinfeel function.

Smaller amounts of co-surfactants may also be included in compositions of the present invention. One useful surfactant is an ethoxylated castor oil, preferably an ethoxylated hydrogenated castor oil. The moles of ethylene oxide per mole of castor oil will range from about 30 to about 55, preferably between about 37 and about 43, optimally about 40 moles of ethylene oxide. Amounts of the ethoxylated castor oil will range from about 0.1 to about 20%, preferably from about 1 to about 10%, optimally from about 2 to about 5% by weight of the composition. Most preferred is PEG-40 hydrogenated castor oil.

Another useful co-surfactant is that of a propoxylated alkyl ether. The ether will be based upon a $C_4$–$C_{20}$ mono- or dihydric alkanol. Most preferred are the propoxylated butyl and cetyl alcohols and butanediols. The amount of propylene oxide per mole of alkanol will range from about 5 to about 50, preferably from about 8 to about 20, optimally from about 8 to about 12 moles propylene oxide. Amounts of the propoxylated alkyl ether will range from about 0.1 to about 10%, preferably from about 1 to about 8%, optimally from about 2 to about 5% by weight of the composition. Most preferred are the species PPG-10 cetyl ether and PPG-14 butyl ether and PPG-10 butanediol.

Particularly preferred as a co-surfactant is a combination of PPG 26 buteth 26 and PEG 40 hydrogenated castor oil sold as a combination under the trademark Solubilisant LRI by Wackherr SA, France. Amounts of Solubilisant LRI may range from 1 to 10% by weight.

Silicones may also usefully be incorporated into compositions according to the present invention. Particularly preferred are silicone copolyol waxes such as DC 2501, commercially available from the Dow Corning Company. The silicone waxes are useful for imparting a smooth feel to the compositions and may be present in amounts from about 0.1 to 5%, preferably from about 0.5 to 3%, optimally from about 1 to about 2% by weight.

Silicone oils may also be incorporated in compositions of the present invention. These may either be volatile or nonvolatile. Volatile silicone oils are preferably chosen from cyclic or linear polydimethylsiloxanes containing from about 3 to about 9, preferably from about 4 to about 5, silicon atoms. Examples of such materials are Dow Corning 344 and Dow Corning 345. Nonvolatile silicone oils are exemplified by the polyalkyl siloxanes, polyalkylaryl siloxanes and polyether siloxane copolymers. Cetyl dimethicone copolyol and cetyl dimethicone are particularly preferred because these materials also function as emulsifiers and emollients. Silicone oils when present may range in amounts from about 1 to about 50%, preferably from about 2 to about 25% by weight.

In some formulations according to the present invention a thickener will be utilized. Representative of this group are the polyacrylics, such as polyacrylates crosslinked with allyl sucrose commercially available as Carbopol® 934 from the B. F. Goodrich Company of Akron, Ohio, and polyacrylic acid commercially available as Sythalon N from the Three V Company, Weehawken, N.J.. Amounts of the thickener will range from about 0.05 to about 5%, preferably from about 0.1 to about 2%, optimally from about 0.2 to about 0.4% by weight.

Fatty alcohols and fatty acids having from 10 to 20 carbon atoms may also be present in compositions of this invention. Suitable examples include cetyl alcohol or acid, myristic alcohol or acid, palmitic alcohol or acid, stearic alcohol or acid, isostearic alcohol or acid, oleyl alcohol or acid and combinations thereof. Amounts may range from 0.1 to 10% by weight.

Humectants of the polyhydric alcohol type may be included in the aqueous phase of compositions according to the present invention. Amounts of the humectant may range from about 0.5 to about 10% by weight of the cosmetic composition. Illustrative of this category are propylene glycol, dipropylene glycol, polyethylene glycol, sorbitol, glycerin and mixtures thereof.

Preservatives are usually incorporated into cosmetic compositions of this invention at levels ranging from 0.01 to 3%, preferably from about 0.3 to about 2%, optimally from about 0.8 to about 1.2% by weight. Particularly preferred preservatives are methylparaben, propylparaben, disodium edetate, 2-phenoxyethanol, imidazolidinyl urea and combinations thereof.

Minor adjunct ingredients may also be present in amounts each from 0.01 to 2%. These include antioxidants (e.g.

butylated hydroxytoluene), antifoam agents, opacifiers and colorants, each in an effective amount to accomplish their respective functions.

The following examples will more fully illustrate the embodiments of this invention. All parts, percentages and proportions referred to herein and in the appended claims are by weight of the cosmetic composition unless otherwise indicated.

EXAMPLES

The following Table outlines a series of cosmetic compositions tested to evaluate the effects of different components and concentrations on the properties of clarity and skinfeel.

TABLE

| COMPONENT | FORMULATION (WEIGHT %) | | | | | | | | |
|---|---|---|---|---|---|---|---|---|---|
| | 1 | 2 | 3 | 4 | 5 | 6 | 7 | 8 | 9 |
| Labrasol* | 3 | — | — | 1 | — | 20 | 30 | 30 | 28 |
| Fragrance | 5 | 3 | 3 | 3 | 3 | 3 | 1.5 | 1.5 | 1.5 |
| Permethyl 99A** | — | — | — | — | 1 | 3 | 8 | 7 | 9.5 |
| Solubilisant LRI*** | 8 | 6 | 8 | 6 | 6 | 8 | 5 | 5 | 4.5 |
| DC 2501 | 1 | — | — | — | — | 1.5 | 1.5 | 1.5 | 1.5 |
| Water | 83 | 91 | 89 | 90 | 90 | 64.5 | 54.5 | 55 | 55 |
| Properties | | | | | | | | | |
| Clarity | Clear | V. Slightly Milky | Clear | V. Slightly Milky | Very Milky | Clear | Initially Clear but Cloudy after 3 hours | Clear | Clear |
| Skinfeel | Draggy | Tacky | Tacky | Less Tacky than #2 | Less Tacky than #2 | Excellent | — | — | — |

*PEG-8 Caprylic/Capric Glycerides
**Isoeicosane
***PPG-26 Buteth-26/PEG-40 Hydrogenated Castor Oil Formulations 1 and 6–8 establish that clarity is improved in the presence of PEG-8 Caprylic/Capric Glycerides. These results are in contrast to the milky characteristics obtained in Formulations 2 and 5 where Labrasol® is absent.

The presence of isoeicosane (Permethyl 99A) significantly contributed to improved skinfeel in Formulation 5 as compared to Formulation 2.

Although this invention is described with reference to specific Examples, it would be apparent to one skilled in the art that various modifications may be made thereto which fall within the spirit and purview of this invention.

What is claimed is:

1. A cosmetic clear microemulsion composition comprising:

(i) from 0.5 to 8% by weight of a fragrance;

(ii) from 30 to 80% of water;

(iii) from 0.5 to 8% by weight of isoeicosane; and (iv) from 1 to 40% by weight of a caprylic/capric fatty glyceride ester ethoxylated with from 1 to 100 moles ethylene oxide per mole of glyceride.

2. A composition according to claim 1 wherein the fragrance has a scent identical to a scent of a commercial signature perfume.

3. A composition according to claim 1 wherein the fragrance is formed of components selected from the group consisting of $C_{10}$–$C_{30}$ terpenes, $C_5$–$C_{50}$ aldehydes, $C_5$–$C_{50}$ ketones, $C_5$–$C_{50}$ esters and combinations thereof.

4. A composition according to claim 1 further comprising from 0.1 to 20% of hydrogenated castor oil ethoxylated with about 30 to about 55 moles of ethylene oxide per mole of castor oil.

5. A composition according to claim 1 further comprising from 0.1 to 10% of a $C_4$–$C_{20}$ mono- or di- hydric alkanol propoxylated with about 5 to about 50 moles of propylene oxide per mole of alkanol.

6. A composition according to claim 1 further comprising from 0.1 to 5% of a silicone wax.

* * * * *